United States Patent
Pham et al.

[11] Patent Number: 6,001,796
[45] Date of Patent: Dec. 14, 1999

[54] AZEOTROPE-LIKE COMPOSITIONS OF 1,1,1,3,3-PENTAFLUOROPROPANE AND HYDROGEN FLUORIDE

[75] Inventors: Hang Thanh Pham, Amherst; Rajiv Ratna Singh, Getzville; Ian Robert Shankland, Williamsville; Hsueh Sung Tung, Getzville, all of N.Y.

[73] Assignee: AlliedSignal Inc., Morristown, N.J.

[21] Appl. No.: 08/675,019

[22] Filed: Jul. 3, 1996

[51] Int. Cl.[6] .................................. C11D 7/30; C11D 7/50
[52] U.S. Cl. ........................... 510/408; 570/164; 570/165
[58] Field of Search ........................... 510/408; 570/164, 570/165

[56] References Cited

U.S. PATENT DOCUMENTS

| | | | |
|---|---|---|---|
| 4,944,846 | 7/1990 | Manzer et al. | 203/1 |
| 5,094,773 | 3/1992 | Manzer et al. | 252/172 |
| 5,409,625 | 4/1995 | Nappa et al. | 252/67 |
| 5,461,177 | 10/1995 | Manzer et al. | 570/178 |
| 5,574,192 | 11/1996 | VanDerPuy et al. | 570/167 |
| 5,616,819 | 4/1997 | Boyce et al. | 570/167 |

FOREIGN PATENT DOCUMENTS

| | | |
|---|---|---|
| 684687 | 4/1964 | Canada. |
| WO94/27939 | 12/1994 | WIPO. |
| 95/04022 | 2/1995 | WIPO. |
| WO95/32935 | 12/1995 | WIPO. |
| WO97/05089 | 2/1997 | WIPO. |
| WO97/27163 | 7/1997 | WIPO. |

OTHER PUBLICATIONS

Jürgen Gmehling et al,*Azeotropic Data*. Part I. VCH, Weinheim (1994) no month available, Introduction.

*Advances in Chemistry Series* vol. 6 "Azeotropic Data", American Chemical Society, Jun. 1952. pp. 50–51.

*Primary Examiner*—Christine Skane
*Attorney, Agent, or Firm*—Jay P. Friedenson; Marie Collazo

[57] ABSTRACT

Provided are azeotropic and azeotrope-like mixtures of 1,1,1,3,3-pentafluoropropane (HFC-245fa) and hydrogen fluoride. Such are useful as an intermediate in the production of HFC-245fa. The latter is useful as a nontoxic, zero ozone depleting fluorocarbon useful as a solvent, blowing agent, refrigerant, cleaning agent, aerosol propellant, heat transfer medium, dielectric, fire extinguishing composition and power cycle working fluid.

13 Claims, 2 Drawing Sheets

T = 20°C

AZEOTROPE-LIKE COMPOSITIONS OF 1,1,1,3,3-PENTAFLUOROPROPANE AND HYDROGEN FLUORIDE

BACKGROUND OF THE INVENTION

1. Field of the Invention

The present invention pertains to azeotropic and azeotrope-like compositions of 1,1,1,3,3-pentafluoropropane (HFC-245fa) and hydrogen fluoride.

2. Description of the Prior Art

In recent years there has been universal concern that completely halogenated chlorofluorocarbons (CFC's) might be detrimental to the Earth's ozone layer. Consequently, there is a worldwide effort to use fluorine-substituted hydrocarbons which contain fewer or no chlorine substituents. In this regard, 1,1,1,3,3-pentafluoropropane, a hydrofluorocarbon (HFC) having zero ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are also non-flammable, and non-toxic as compared to the chlorine containing compounds.

HFC-245fa is well known in the art as described in U.S. Pat. No. 2,942,036, Canadian 684,687, EP 381 986A, JP 02,272,086 and WO 95/04022. All of the foregoing patents are incorporated herein by reference.

It has now been found that an important intermediate in the production of substantially pure 1,1,1,3,3-pentafluoropropane, is an azeotrope or azeotrope-like mixture of 1,1,1,3,3-pentafluoropropane and hydrogen fluoride. This intermediate, once formed, may thereafter be separated into its component parts by extraction techniques, even though they have close boiling points. HFC-245fa has a boiling point of about 14° C. and HF has a normal boiling point of about 20° C. at standard atmospheric pressure, which makes it particularly useful as a blowing agent or aerosol propellant. The azeotropic and azeotrope-like compositions find use not only as intermediates in the production of HFC-245fa, but they are additionally useful as solvents, as well as compositions for removing surface oxidation from metals. In addition, the formation of an azeotropic or azeotrope-like composition of 1,1,1,3,3-pentafluoropropane and hydrogen fluoride is useful in separating a mixture of 1,1,1,3,3-pentafluoropropane and an impurity such as 1,1,1-trichloro-4,4-dichlorobutane (HCC-240fa). When it is desired to separate a mixture of 1,1,1,3,3-pentafluoropropane and an impurity, HF is added to form an azeotropic mixture of 1,1,1,3,3-pentafluoropropane and hydrogen fluoride, and then the impurity is removed from the azeotropic mixture, such as by distillation, scrubbing or other known means.

SUMMARY OF THE INVENTION

The invention provides an azeotropic composition consisting essentially of 1,1,1,3,3-pentafluoropropane and hydrogen fluoride.

The invention further provides an azeotropic or azeotrope-like composition which consists essentially of from about 1 to about 50 weight percent hydrogen fluoride and from about 50 to about 99 weight percent 1,1,1,3,3-pentafluoropropane, which composition has a boiling point of from about 14° C. to about 75° C. at a pressure of from about 14.6 psia to about 142 psia.

The invention also provides a method of forming an azeotropic or azeotrope-like composition which consists essentially of blending from about 1 to about 50 weight percent hydrogen fluoride and from about 50 to about 99 weight percent 1,1,1,3,3-pentafluoropropane, which composition has a boiling point of from about 14° C. to about 75° C. at a pressure of from about 14.6 psia to about 142 psia.

The invention still further provides a process for removing 1,1,1,3,3-pentafluoropropane from a mixture containing 1,1,1,3,3-pentafluoropropane and at least one impurity, which comprises adding hydrogen fluoride to the mixture in an amount sufficient to form an azeotropic or azeotrope-like composition of the 1,1,1,3,3-pentafluoropropane and the hydrogen fluoride, and thereafter separating the azeotropic composition from the impurity.

DETAILED DESCRIPTION OF THE PREFERRED EMBODIMENT

Figure 1:
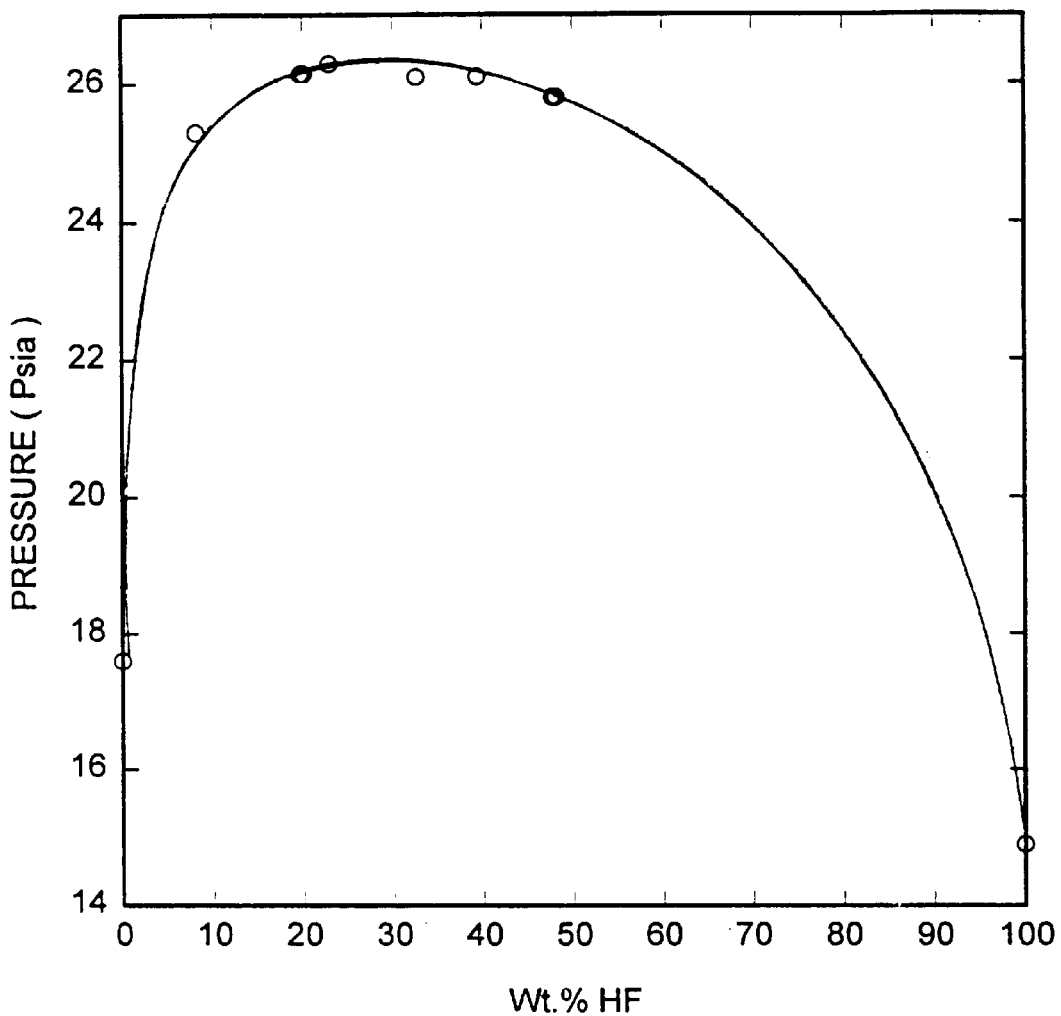
FIG. 1 shows a plot of the vapor pressures of the mixtures formed in Example 3 as measured at 20° C.

In a method of preparing HFC-245fa, precursor reagents are fluorinated with hydrogen fluoride. The reaction products of such precursors include HFC-245fa, unreacted HF and other by-products. Upon removal of the by-products, a binary azeotrope or azeotrope-like composition of HFC-245fa and HF is formed. This binary azeotrope or azeotrope-like composition is then available for separation into its component parts. The azeotropic or azeotrope-like compositions of the HFC-245fa and HF are also useful as recycle to the fluorination reactor. Thus, for example, in a process for producing HFC-245fa, one can recover a portion of the HFC-245fa as an azeotropic or azeotrope-like composition of HFC-245fa and HF and then recycle the composition to the reactor. HFC-245fa forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation. One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance. Another characteristic of azeotrope-like compositions is that there is a range of compositions containing the same components in varying proportions which are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and HFC-245fa to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with HFC-245fa.

In the preferred embodiment, the inventive composition contains from about 1 to about 50 weight percent HF, preferably from about 10 weight percent to about 40 weight percent and most preferably from about 15 weight percent to about 30 weight percent. In the preferred embodiment, the inventive composition contains from about 50 to about 99 weight percent HFC-245fa, preferably from about 60 weight percent to about 90 weight percent and most preferably from about 70 weight percent to about 85 weight percent. The composition of the present invention has a boiling point of from about 14° C. to about 75° C. at a pressure of from about 14.6 psia to about 142 psia. An azeotropic or azeotrope-like composition having about 27±5 weight percent HF and about 73±5 weight percent HFC-245fa has been found to boil at about 14° C. and 14.6 psia. An azeotropic or azeotrope-like composition of about 25±5 weight percent HF and about 75±5 weight percent HFC-245fa has been found to boil at 20° C. and 26 psia. An azeotropic or azeotrope-like composition of about 17±5 weight percent HF and about 83± weight percent HFC-245fa has been found to boil at 75° C. and 142 psia.

In another embodiment of the invention, 1,1,1,3,3-pentafluoropropane may be removed from a mixture containing 1,1,1,3,3-pentafluoropropane and an impurity which may, for example, result from manufacturing steps in the preparation of 1,1,1,3,3-pentafluoropropane. This is done by adding hydrogen fluoride to the mixture of the 1,1,1,3,3-pentafluoropropane and impurity. Hydrogen fluoride is added to the mixture in an amount sufficient to form an azeotropic composition of the 1,1,1,3,3-pentafluoropropane and the hydrogen fluoride, and thereafter the azeotropic composition is separated from the impurity, for example by distillation, scrubbing, or other art recognized separating means. Preferably, the impurity itself does not form an azeotropic mixture with 1,1,1,3,3-pentafluoropropane, hydrogen fluoride or a mixture of 1,1,1,3,3-pentafluoropropane and hydrogen fluoride. Typical impurities include other halocarbons which may be miscible with 1,1,1,3,3-pentafluoropropane such as HCC-240fa.

The following non-limiting examples serve to illustrate the invention.

EXAMPLE 1

Approximately 400 pounds of antimony pentachloride catalyst is charged into a 50 gallon reactor. The reactor temperature is raised to 95° C. About 25 lbs/hour of HCC-240fa, 15 lbs/hour of HF and 2 lbs/hour of chlorine are fed to the reactor continuously. Chlorine is used to keep the catalyst active. The reactor pressure is maintained at about 200 psig. The product stream contains HFC-245fa, HF, HCl and organic by-products such as 1,3,3,3-tetrafluoropropene, 1-chloro-3,3,3-trifluoropropene, and 1-chloro-3,3,3-tetrafluoropropene among others. About 21 lbs/hour of HCl is then removed from the product stream by low temperature distillation. Organic by-products are removed by distillation.

EXAMPLE 2

73 g of 1,1,1,3,3-pentafluoropropane (HFC-245fa) were dissolved in 27 g of HF to form a homogeneous azeotrope mixture. This experiment was done at 14° C. at 14.6 psia.

EXAMPLE 3

75 g of 1,1,1,3,3-pentafluoropropane (HFC-245fa) were dissolved in 25 g of HF to form a homogeneous mixture. This experiment was done at room temperature (25° C.).

EXAMPLE 4

58.7 g of 1,1,1,3,3-pentafluoropropane (HFC-245fa) are dissolved in 20.1 g of HF to form a homogeneous mixture. This experiment is done at room temperature (25° C.).

EXAMPLE 5

Binary compositions containing solely 1,1,1,3,3-pentafluoropropane (HFC-245fa) and HF are blended to form homogeneous azeotrope mixtures having different compositions. The vapor pressures of the mixtures are measured at 20° C. and 75° C. and the following results are noticed.

Table 1 shows the vapor pressure measurement of HFC-245fa and HF as a function of composition of weight percent HF at two constant temperatures of 20° C. and 75° C. From this table it is observed that at 20° C. the composition at which the vapor pressure is maximum is about 23.1 weight percent HF or between 19.9 and 32.7 weight percent HF. At 75° C., the composition at which the vapor pressure is maximum is about 19.9 weight percent HF or between 8.3 and 23.1 weight percent HF. From this example it is determined that the azeotropic composition is about 23.1 weight percent HF at 20° C. and about 19.9 weight percent HF at 75° C.

TABLE 1

| WEIGHT PERCENT HF | PRESSURE (PSIA) | |
|---|---|---|
| | T = 20° C. | T = 75° C. |
| 0.0 | 17.6 | 100.3 |
| 8.3 | 25.3 | 138.9 |
| 19.9 | 26.2 | 141.8 |
| 23.1 | 26.3 | 141.6 |
| 32.7 | 26.1 | 138.9 |
| 39.5 | 26.1 | 136.6 |
| 47.9 | 25.8 | 133.3 |
| 100.0 | 14.9 | 81.4 |

The data also show that the vapor pressure of mixtures of HFC-245fa and HF is higher, at all indicated blend proportions, than HFC-245fa and HF alone, i.e. as indicated in the first and last rows when HF is 0.0 wt. % and HFC-245fa is at 100.0 wt. % as well as when HFC-245fa is at 0.0 wt. % and HF is at 100.0 wt. %.

The azeotropic compositions of HFC-245fa and HF may also be verified by vapor-liquid equilibrium (VLE) measurements. The liquid and vapor of the mixtures are sampled at about 16, 20, 30 and 50±5 weight percent HF at 20° C. and 75° C. At 75° C. it is determined that the liquid and vapor compositions are about the same at about 16±5 weight percent HF. At 20° C. it is determined that the liquid and vapor compositions are about the same at about 25±5 weight percent HF.

TABLE 2

| TEMPERATURE | | COMPOSITIONS (WEIGHT PERCENT HF, ±3%) | |
|---|---|---|---|
| ° C | PRESSURE (PSIA) | LIQUID | VAPOR |
| 19.8 | 25.8 | 48.3 | 27.8 |
| 74.6 | 132.8 | 53.0 | 24.5 |
| 19.8 | 26.1 | 32.7 | 27.5 |
| 19.8 | 26.2 | 20.2 | 23.9 |
| 74.6 | 141.8 | 15.9 | 16.2 |

Figure 2:
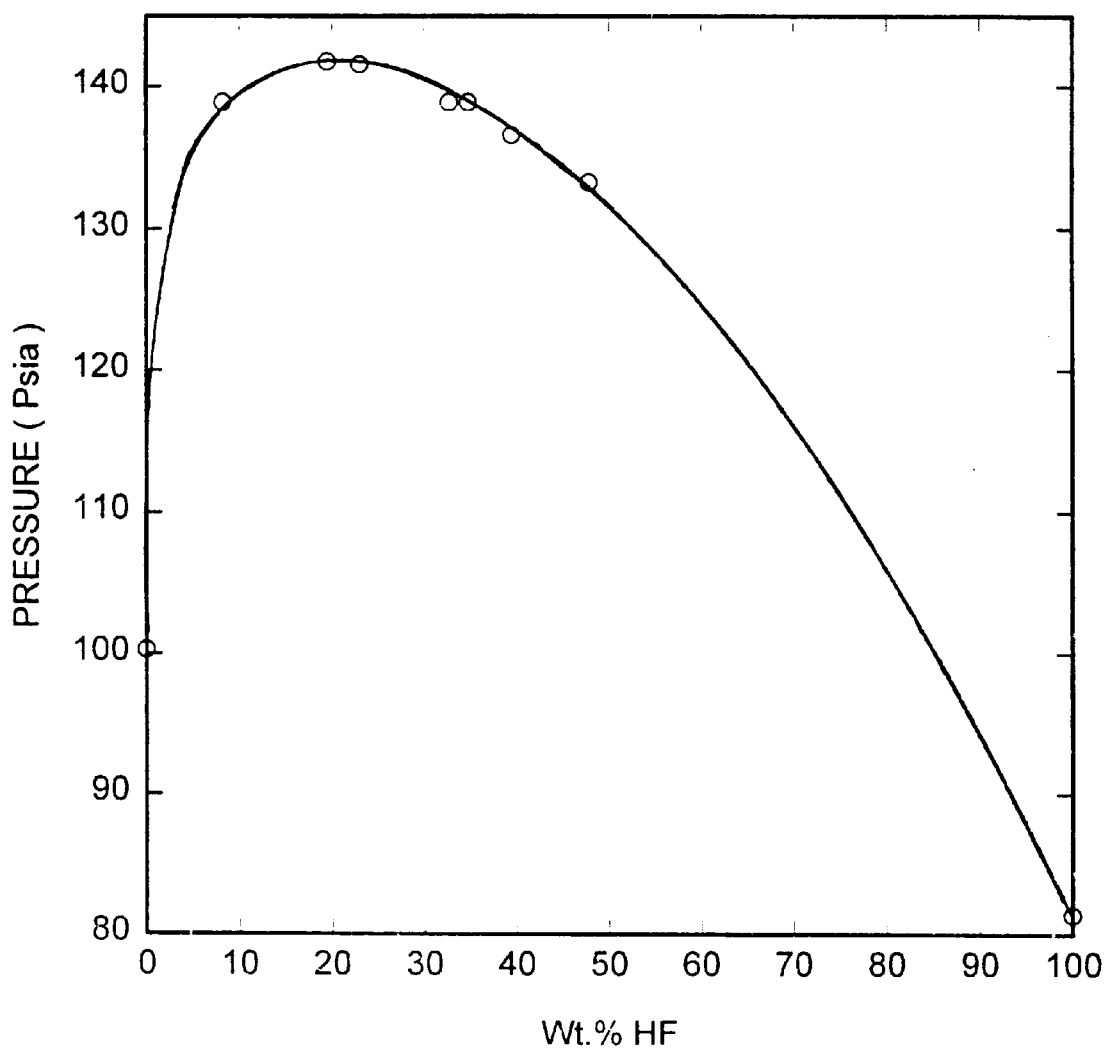
FIG. 2 shows a plot of the vapor pressures of the mixtures formed in Example 3 as measured at 75° C.

A comparison of the data from Tables 1 and 2 indicates that the vapor-liquid equilibrium results from Table 2 are in agreement with the vapor pressure measurements of Table 1. The data from Table 1 are shown in graphic form in FIGS. 1 and 2.

What is claimed is:

1. An azeotrope-like composition which consists essentially of from about 1 to about 50 weight percent hydrogen fluoride and from about 50 to about 99 weight percent 1,1,1,3,3-pentafluoropropane, which composition has a vapor pressure of above 17.6 psia to about 26 psia at about 20° C. or a vapor pressure of above 100.3 psia to about 142 at about 75° C.

2. The composition of claim 1 which consists of hydrogen fluoride and 1,1,1,3,3-pentafluoropropane.

3. The composition of claim 1 wherein the hydrogen fluoride in present in an amount of from about 10 to about 40 weight percent.

4. The composition of claim 1 wherein the hydrogen fluoride in present in an amount of from about 15 to about 30 weight percent.

5. The composition of claim 1 having a boiling point of about 14° C. at a pressure of about 14.6 psia.

6. The composition of claim 1 having a boiling point of about 75° C. at a pressure of about 142 psia.

7. A method of forming an azeotrope-like composition which consists essentially of blending from about 1 to about 50 weight percent hydrogen fluoride and from about 50 to about 99 weight percent 1,1,1,3,3-pentafluoropropane, which composition has a vapor pressure of above 17.3 psia to about 26 psia at about 20° C. or a vapor pressure of above 100.3 psia to about 142 psia at about 75° C.

8. The method of claim 7 wherein the composition consists of hydrogen fluoride and 1,1,1,3,3-pentafluoropropane.

9. The method of claim 7 wherein the hydrogen fluoride in present in an amount of from about 10 to about 40 weight percent.

10. The method of claim 7 wherein the hydrogen fluoride in present in an amount of from about 15 to about 30 weight percent.

11. The method of claim 7 wherein the composition has a boiling point of from about 14° C. at a pressure of about 14.6 psia.

12. The method of claim 7 wherein the composition has a boiling point of from about 75° C. at a pressure of about 142 psia.

13. An azeotrope-like composition in which the azeotrope-like components consist of from about 1 to about 50 weight percent hydrogen fluoride and from about 50 to about 99 weight percent 1,1,1,3,3-pentafluoropropane, which composition has a vapor pressure of above 17.6 psia to about 26 psia at about 20° C. or a vapor pressure of above 100.3 psia to about 142 at about 75° C.

* * * * *